US008252922B2

(12) United States Patent
Wang et al.

(10) Patent No.: US 8,252,922 B2
(45) Date of Patent: *Aug. 28, 2012

(54) METHOD FOR CRYSTALLIZING SUCRALOSE

(75) Inventors: Fei Wang, Nanjing (CN); Haibing He, Nanjing (CN); Jinshan Wu, Yancheng (CN); Xin Yang, Nanjing (CN); Yongzhu Yu, Nanjing (CN); Zhisong Fan, Nanjing (CN)

(73) Assignee: JK Sucralose Inc., Yancheng, Jiangsu Province (CN)

( * ) Notice: Subject to any disclaimer, the term of this patent is extended or adjusted under 35 U.S.C. 154(b) by 557 days.

This patent is subject to a terminal disclaimer.

(21) Appl. No.: 11/744,335

(22) Filed: May 4, 2007

(65) Prior Publication Data

US 2008/0221312 A1 Sep. 11, 2008

(30) Foreign Application Priority Data

Mar. 6, 2007 (CN) .......................... 2007 1 0085646

(51) Int. Cl.
*C07H 1/06* (2006.01)
*C07H 1/08* (2006.01)

(52) U.S. Cl. ..................................................... 536/127

(58) Field of Classification Search .................. None
See application file for complete search history.

(56) References Cited

U.S. PATENT DOCUMENTS

| 4,343,934 A | 8/1982 | Jenner et al. |
| 4,380,476 A | 4/1983 | Mufti et al. |
| 4,751,294 A * | 6/1988 | Jackson ........................ 536/122 |
| 4,783,526 A | 11/1988 | O'Brien et al. |
| 4,977,254 A | 12/1990 | Homer et al. |
| 5,141,860 A | 8/1992 | Bornemann et al. |
| 5,298,611 A | 3/1994 | Navia et al. |
| 5,498,709 A | 3/1996 | Navia et al. |
| 6,943,248 B2 | 9/2005 | Catani et al. |
| 2006/0188629 A1 * | 8/2006 | Liesen et al. .................. 426/548 |
| 2008/0161552 A1 * | 7/2008 | Wang et al. .............. 536/123.13 |

OTHER PUBLICATIONS

Ault, Techniques and Experiments for Organic Chemistry, Edition 6, University Science Books 1998, pp. 43-62.*
Vogel, Practical Organic Chemistry, Third Edition, Longman Group Limited 1956, pp. 122-139.*

* cited by examiner

*Primary Examiner* — Layla Bland
(74) *Attorney, Agent, or Firm* — Occhiuti Rohlicek & Tsao LLP

(57) ABSTRACT

The present application discloses a method for crystallizing sucralose, which uses an alcohol solvent or a mixed solvent of alcohol and other solvent(s) in the crystallization of sucralose.

15 Claims, No Drawings

METHOD FOR CRYSTALLIZING SUCRALOSE

CROSS-REFERENCE TO RELATED APPLICATIONS

This application is being filed as a U.S. Utility application which claims the benefit of Chinese Patent Application No. 200710085646.4, filed on Mar. 6, 2007, the contents of which is hereby incorporated by reference in its entirety.

FIELD OF THE INVENTION

The present invention relates to a method for crystallizing sucralose.

BACKGROUND OF THE INVENTION

As a novel sweetener, sucralose is derived from sucrose by replacing the hydroxyls in the 4, 1' and 6' positions with chlorine. Its sweetness is 600 times of sucrose. Sucralose does not take part in human metabolism, thus has high safety and high resistance to acid hydrolysis. These advantages allow it being the most favorable highly effective sweetener, and are approved by more than thirty countries for use already. Patents of U.S. Pat. Nos. 4,343,934, 5,141,860, 4,977,254, 4,783,526, 4,380,476, 5,298,611 and so on illustrate a method for crystallizing sucralose, which use water as solvent for crystallization. The disadvantages of the method comprise: crystallization time is too long, which usually need several day; crystallization is incomplete, thus the crystallization mother liquor generally contains a large amount of sucralose, and the recovery of the mother liquor is relatively complicated; the product has relatively high moisture content, which adversely influences the stability of the product. U.S. Pat. No. 5,498,709 discloses a method for crystallizing sucralose, which uses ethyl acetate as the crystallization solvent. However, this method also has the problem of long crystallization time and low yield for the first operation. U.S. Pat. No. 6,943,248 provides a method for crystallizing sucralose, which uses a mixed solvent of methanol and ethyl acetate. However, owing to the too close boiling points of these solvents, it is difficult to separate out methanol and thereby obtain crystalline sucralose from ethyl acetate via simple distilling apparatuses. In this regard, U.S. Pat. No. 6,943,248 utilizes evaporating pipes to achieve the separation of methanol and ethyl acetate. However, the use of this apparatus is liable to leads to precipitation of sucralose in the pipeline, which renders further processes difficult to be continued. Consequently, it is obvious that this method is not suitable for industrial production.

SUMMARY OF THE INVENTION

Aiming at the shortages of the foregoing crystallization methods, the purpose of present invention is to provide a crystallization method with higher yield, more simple apparatus and even better product quality.

In order to achieve the aforementioned purpose, the present invention provides a method for crystallizing sucralose, which comprises: adding the sucralose solid or sucralose concentrate to be purified into a solvent, heating the mixture thus obtained to completely dissolve sucralose, then slowly cooling down the solution thus obtained and allowing it to stand and crystallize, and obtaining crystalline sucralose after filtrating and drying; wherein the solvent used in the crystallization is an alcohol solvent or a mixed solvent of alcohol and other solvent(s).

In the method of the present invention, the alcohol solvent use for the crystallization of sucralose is preferably selected from a group consisted of methanol, ethanol and isopropanol. However, one skilled in the art would understand that useful alcohol solvents are not limited to the above solvents.

In the method of the present invention, the solvent used for the crystallization of sucralose may be a alcohol solvent or a mixed solvent of alcohol and other solvent(s).

In case of using a mixed solvent of alcohol and other solvent(s), said other solvent(s) used in the mixed solvent may be selected from a group consisted of ethyl acetate, propyl acetate, isopropyl acetate, butyl acetate and acetone.

The volume ratio of the sucralose solid or concentrate to the solvent can be determined conveniently according to the selected specific solvent. In general, the volume ratio of sucralose solid or sucralose concentrate to solvent may be set in a range of from about 1:1 to about 1:6.

In the method of the present invention, after the dissolution of sucralose, a part of solvent may be removed by concentrating before crystallization by cooling.

The temperature for the dissolution of sucralose can be appropriately selected according to dissolving conditions, generally being about 65 to about 80° C.

In the method of the present invention, the temperature for standing crystallization is generally about −5° C. to about 30° C.

In the method of the present invention, the volume ratio of alcohol to other solvent(s) in the mixed solvent can be appropriately determined in a wide range according to the specifically selected solvents, usually the volume ratio of alcohol to other solvent(s) in the mixed solvent is in a range of from about 1:0.5 to about 1:3.

The method for crystallizing sucralose of the present invention goes as follows: firstly, sucralose solution obtained from reaction is concentrated to obtain a syrup or crude sucralose in solid form; then add the sucralose solid or sucralose concentrate into the solvent used for crystallization, and the mixture thus obtained is heated to completely dissolve sucralose; then active carbon is added into the solution thus obtained to decolorize the sucralose solution; then the solution is filtrated, and the filtrate is slowly cooled down and allowed to stand and crystallize; at last crystalline sucralose is obtained after filtrating and drying.

Compared with the reported method for crystallizing sucralose, the present invention has the advantages of lower cost, higher yield, simpler apparatuses, lower cost and so on.

The present invention will be further illustrated by the following examples, which however will not limit the present invention.

EXAMPLE 1

Sucralose (100 ml solution in methanol) was obtained from a deacylation reaction by using 20 g of trichlorosucrose-6-ethyl ester as the raw material. The sucralose solution was concentrated to obtain dry solid. The solid thus obtained was added into 60 g of anhydrous alcohol. The mixture was heated to 75° C. with stirring to completely dissolve sucralose. 0.5 g of active carbon was added in to the solution thus obtained, and then the solution was stirred for 15 minutes followed by filtration. The filtrate was concentrated under vacuum until 40 g of ethanol was distilled off, then cooled down to room temperature over about 5 hours, and allowed to stand for 3 hours and crystallize. 15 g crystalline sucralose was obtained after filtrating and drying under vacuum.

EXAMPLE 2

Sucralose (100 ml solution in methanol) was obtained from a deacylation reaction by using 20 g of trichlorosucrose-6-ethyl ester as the raw material. The sucralose solution was concentrated to obtain dry solid. The solid thus obtained was added into 55 ml of a mixed solvent consisting of methanol and ethyl acetate in a ratio of 1:2. The mixture was heated to reflux to completely dissolve sucralose. 0.5 g of active carbon was added into the solution thus obtained, then the solution was stirred for 15 minutes followed by filtration. The filtrate was cooled down to 0° C. over 5 hours, and allowed to stand for 5 hours and crystallize. 15.5 g crystalline sucralose was obtained after filtrating and drying under vacuum.

EXAMPLE 3

20 g of sucralose crude product (with a purity of 96%) was added into 50 ml of a mixed solvent consisting of methanol and propyl acetate in a ratio of 1:1. The mixture was heated to reflux to completely dissolve sucralose. 0.5 g of active carbon was added in to the solution thus obtained, and then the solution was stirred for 15 minutes followed by filtration. The filtrate was cooled down to 5° C. over 6 hours, and allowed to stand for 3 hours and crystallize. 15.8 g crystalline sucralose (with a purity of 98.5%) was obtained after filtrating and drying under vacuum.

EXAMPLE 4

20 g of sucralose crude product (with a purity of 96%) was added into 100 ml of a mixed solvent consisting of ethanol and acetone in a ratio of 1:3. The mixture was heated to reflux to completely dissolve sucralose. 0.5 g of active carbon was added in to the solution thus obtained, and then the solution was stirred for 15 minutes followed by filtration. The filtrate was cooled down to 10° C. over 5 hours, and allowed to stand for 3 hours and crystallize. 14.2 g crystalline sucralose (with a purity of 98.7%) was obtained after filtrating and drying under vacuum.

What is claimed is:

1. A method for crystallizing sucralose consisting of: providing a solution of crude sucralose in methanol, evaporating the methanol to obtain a sucralose solid or a sucralose concentrate,
    adding the sucralose solid or the sucralose concentrate into a solvent to obtain a mixture,
    heating the mixture thus obtained to completely dissolve sucralose to obtain a solution,
    slowly cooling down the solution thus obtained,
    allowing the solution thus cooled to stand and crystallize, and
    removing the solvent by filtration and drying to obtain crystalline sucralose, wherein the solvent is an alcohol.

2. The method according to claim 1, wherein the alcohol is selected from a group consisting of methanol, ethanol, and isopropanol.

3. The method according to claim 1, wherein the volume ratio of sucralose solid or sucralose concentrate to the solvent is in a range of from about 1:1 to about 1:6.

4. The method according to claim 1, wherein the temperature for dissolving sucralose is about 65° C. to about 80° C.

5. The method according to claim 1, wherein the temperature for standing and crystallizing is set at about −5° C. to about 30° C.

6. A method for crystallizing sucralose consisting of: providing a solution of crude sucralose in methanol, evaporating the methanol to obtain a sucralose solid or a sucralose concentrate,
    adding the sucralose solid or the sucralose concentrate into a solvent to obtain a mixture,
    heating the mixture thus obtained to completely dissolve sucralose to obtain a solution,
    treating the solution thus obtained with active carbon by stirring followed by filtration,
    slowly cooling down the solution thus treated,
    allowing the solution thus cooled to stand and crystallize, and
    removing the solvent by filtration and drying to obtain crystalline sucralose, wherein the solvent is an alcohol.

7. The method according to claim 6, wherein the alcohol is selected from a group consisting of methanol, ethanol, and isopropanol.

8. The method according to claim 6, wherein the volume ratio of sucralose solid or sucralose concentrate to the solvent is in a range of from about 1:1 to about 1:6.

9. The method according to claim 6, wherein the temperature for dissolving sucralose is about 65° C. to about 80° C.

10. The method according to claim 6, wherein the temperature for standing and crystallizing is set at about −5° C. to about 30° C.

11. A method for crystallizing sucralose consisting of: providing a solution of crude sucralose in methanol, evaporating the methanol to obtain a sucralose solid or a sucralose concentrate,
    adding the sucralose solid or the sucralose concentrate into a solvent to obtain a mixture,
    heating the mixture thus obtained to completely dissolve sucralose to obtain a solution,
    treating the solution thus obtained with active carbon by stirring followed by filtration,
    removing by distillation under vacuum part of the solvent to concentrate the solution thus treated,
    slowly cooling down the solution thus concentrated,
    allowing the solution thus cooled to stand and crystallize, and
    removing the solvent by filtration and drying to obtain crystalline sucralose, wherein the solvent is an alcohol.

12. The method according to claim 11, wherein the alcohol is selected from a group consisting of methanol, ethanol, and isopropanol.

13. The method according to claim 11, wherein the volume ratio of sucralose solid or sucralose concentrate to the solvent is in a range of from about 1:1 to about 1:6.

14. The method according to claim 11, wherein the temperature for dissolving sucralose is about 65° C. to about 80° C.

15. The method according to claim 11, wherein the temperature for standing and crystallizing is set at about −5° C. to about 30° C.

* * * * *